United States Patent
Wadstein

[11] Patent Number: 5,613,955
[45] Date of Patent: Mar. 25, 1997

[54] DEVICE FOR ADMINISTRATION OF FLUID

[75] Inventor: Jan Wadstein, Malmou, Sweden

[73] Assignee: Scandfast AB, Sweden

[21] Appl. No.: 432,195

[22] PCT Filed: Nov. 5, 1993

[86] PCT No.: PCT/SE93/00924

§ 371 Date: May 4, 1995

§ 102(e) Date: May 4, 1995

[87] PCT Pub. No.: WO94/11046

PCT Pub. Date: May 26, 1994

[51] Int. Cl.⁶ .................................................. A61M 5/32
[52] U.S. Cl. ............................................ 604/178; 604/280
[58] Field of Search .................................. 604/158, 174, 604/178, 264, 272–274, 280, 283

[56] References Cited

U.S. PATENT DOCUMENTS 4,798,595  1/1989  Andersson et al. .
4,971,076  11/1990  Densert et al. .

FOREIGN PATENT DOCUMENTS 0295397  12/1988  European Pat. Off. .
1196327   7/1965   Germany .
3636806   5/1987   Germany .
445518    6/1986   Sweden .
8403217   8/1984   WIPO .

Primary Examiner—Corrine M. McDermott
Attorney, Agent, or Firm—Merchant, Gould, Smith, Edell, Welter & Schmidt, P.A.

[57] ABSTRACT

The invention relates to an arrangement for the administration of a fluid. The arrangement consists of a tube, preferably made of plastic, one end of which is executed with a cutting or tissue-displacing tip. The other end of the tube has a connection (1b) for an injection syringe or the like. Arranged in the tube is a rigid, elongated body so executed as to facilitate insertion of the tube into human tissue. The tube is sufficiently soft for it to be of essentially the same consistency as the surrounding tissue, in particular the subcutaneous tissue and musculator. It is also sealed at its tip and executed with a number of openings distributed over an area between the tip and the connection. The external surface of the tube is covered with a coating of titanium of sufficient thinness for the tube to retain its soft characteristics. The arrangement also comprises an attachment device (3) so arranged, after insertion of the tube and after withdrawal of the aforementioned rigid body, as to be applied between the ends of the tube in order to produce a rigid connection between same.

2 Claims, 2 Drawing Sheets 5,613,955

DEVICE FOR ADMINISTRATION OF FLUID

BACKGROUND OF THE INVENTION

1. Field of the Invention

The present invention relates to an arrangement for the administration of a fluid consisting of a titanium-coated tube, preferably made of plastic, one end of which is sealed, and the other end has a connection for an injection syringe or the like, which tube is executed with a number of openings distributed over an area between the sealed end and the connection, and a rigid, elongated body arranged in the tube is so executed as to facilitate insertion of the tube into human tissue. The invention also comprises an attachment device for attaching the tube to the patient.

2. Description of the Prior Art

Arrangements of the kind described above are commercially available. Disclosed through DE, A1, 36 36 806 is a plastic tube which is executed with a number of openings distributed over an area between one end and the connection, which arrangement also comprises one sealed end, which is rounded, and a second end with a connection for an injection syringe or similar. One disadvantage of this arrangement is that the plastic tube is neither biocompatible nor antibacterial. This gives rise to infections making their way through the catheter, and to the infiltration of bacteria along the outside of the edge in the area of the wound adjacent to the abdominal cavity, where peritonitis occurs. The rounding of the end of the catheter that is to be introduced into the body also means that the introduction of the catheter into body tissues is perceived by the patient as unnecessarily painful.

Also disclosed, for example through SE, A, 8703694-3, is the surface-coating of plastic tubes with titanium oxide with a view to reducing rejection by the body. One disadvantage associated with these previously disclosed surface-coated tubes is the fact that they become very hard, which, in conjunction with their insertion into muscle tissue, gives rise to contractions in the tissue, which is experienced as both uncomfortable and painful.

Previously disclosed through WO, A1, 84/03217 is an arrangement for the attachment of a catheter or the like to a patient. Attachment is effected by introducing the attachment device for the catheter through the patient's skin. Unlike previously disclosed methods of attachment, this method of attachment is reliable, and the risk of the catheter becoming detached is very small, although it suffers from the significant disadvantage that it is uncomfortable for the patient, who must suffer the introduction of further needles into the body tissue in addition to the introduction of the catheter itself.

SUMMARY OF THE INVENTION

One important object of the present invention is to eliminate or, at any rate, to reduce said disadvantages, and this is achieved in that the tube is sufficiently soft for it to be of essentially the same consistency as the surrounding tissue, in particular the subcutaneous tissue and musculature, in that the sealed end of the tube is executed with a cutting or tissue-displacing tip and is covered on its external surface with a coating of titanium of sufficient thinness for the tube to retain its soft characteristics, and in that the arrangement also comprises an attachment device so arranged, after insertion of the tube and after withdrawal of the aforementioned rigid body, as to be applied between the ends of the hose in order to produce a rigid connection between same.

BRIEF DESCRIPTION OF THE DRAWINGS

The invention is described below in more detail with reference to the accompanying drawing, in which.

DESCRIPTION OF THE PREFERRED EMBODIMENT

Figure 1:
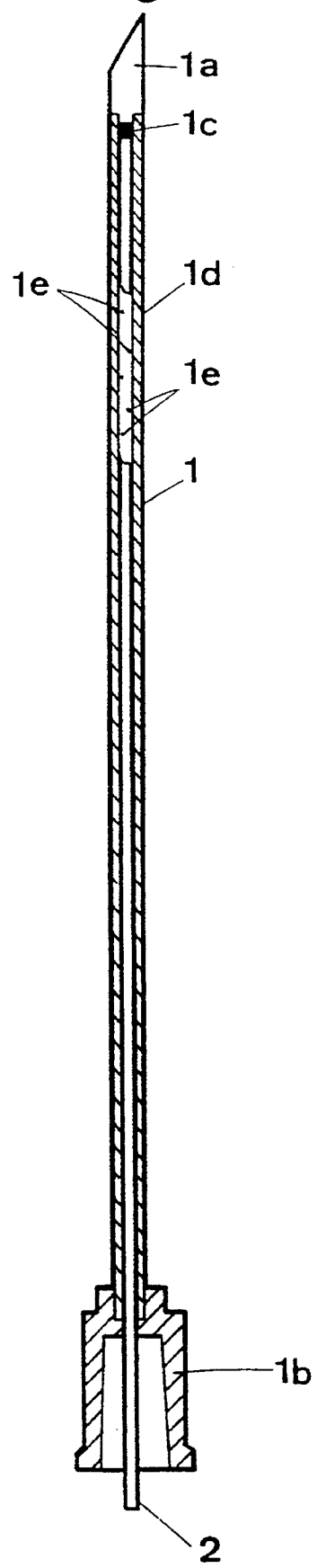
FIG. 1 shows a longitudinal section through a soft needle in accordance with the invention.

In the drawing, the designation 1 is used in respect of a tube, preferably made of plastic and coated with a layer of titanium. The titanium coating is of sufficient thinness (0.002–10 µm) not to affect the softness of the plastic tube. One end of the hose 1 is executed with a cutting tip 1a, and the other end has a connection 1b, for example a so-called Luer cone, for an injection syringe. The tip, which is preferably made of metal and preferably detachable from the tube, can also exhibit a tissue displacing form Arranged inside the tube is a rigid, elongated body 2. This is so arranged as to facilitate insertion of the tube into human tissue.

In accordance with the invention, the tube is sufficiently soft for it to exhibit essentially the same consistency as the surrounding tissue, in particular the subcutaneous tissue and musculature. It is sealed in an area 1c close to the tip 1a and is executed with a number of openings 1e arranged over an area 1d between the tip 1a and the connection 1b, and its outer surface is covered with a coating of titanium.

The arrangement in accordance with the invention also comprises an attachment device 3. This is so arranged, after insertion of the tube 1 and after the rigid body 2 has been withdrawn from the tube 1, as to be applied between the tip 1a and the connection 1b so as to form a rigid connection between same.

Figure 2:
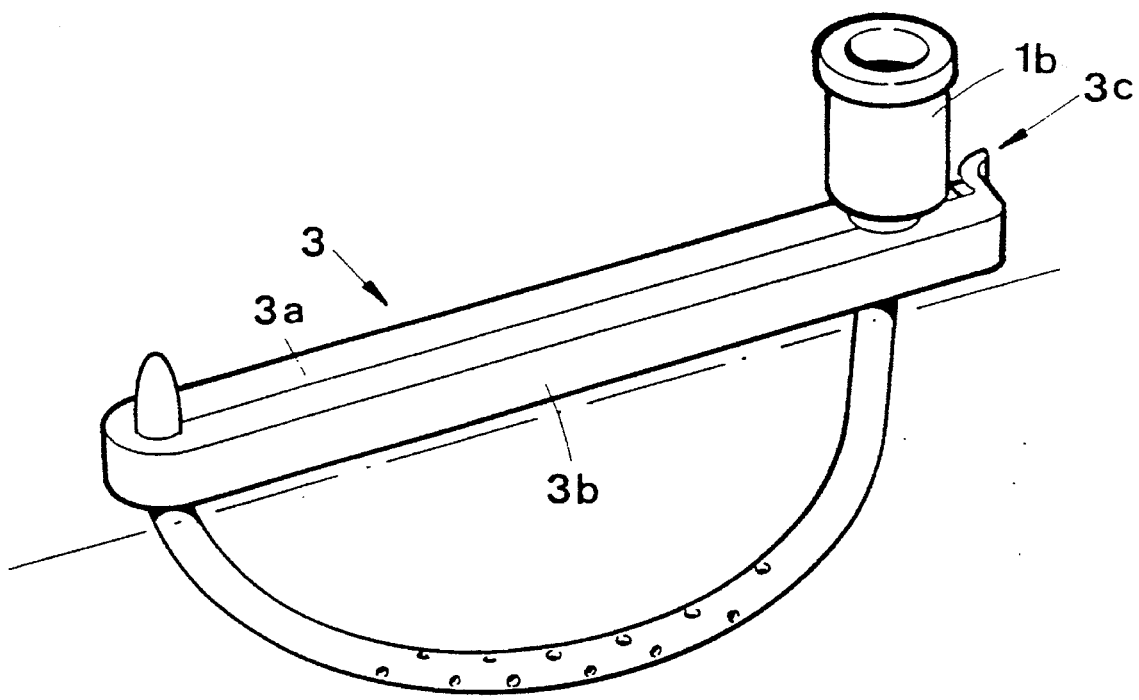
FIG. 2 shows an arrangement in accordance with the invention inserted into human tissue.

The attachment device can be executed in many different ways in order to serve this purpose. In the embodiment illustrated in FIG. 2, the attachment device exhibits two legs 3a, 3b articulated or flexibly connected relative to one another at one end, which legs are provided at their other end with interacting snap devices 3c.

The arrangement in accordance with the invention, which forms a soft needle, is designed for application involving passage through the skin, and the needle 1 is inserted into the tissue with the help of the rigid body 2 at the point where the injection is intended to take place. The cutting or tissue-displacing tip 1a of the needle 1 is also required to force its way up through the skin and then to be attached to the attachment device 3. The rigid body 2 is then withdrawn, and the needle 1 is left in position in the correct tissue.

It is clear that the rigid body 2 can be straight or curved, i.e. it can be varied in its form depending on the actual need.

I claim:

1. An improved arrangement for the administration of a fluid a tube, preferably made of plastic, a first end of which is sealed, and a second end of which has a connection for an injection syringe or the like, and executed with a number of openings distributed over an area between the first end and the connection and a rigid, elongated body arranged in the tube so executed as to facilitate insertion of the tube into human tissue, the improvement comprising:

a tip disposed at the first end of the tube to cut or displace tissue: and an attachment device to hold the first and second ends of the tube after insertion of the tube into tissue and after withdrawal of the rigid body, so as to produce a rigid connection between the first and second ends: wherein the tube is sufficiently soft as to be of essentially the same consistency as the human tissue, in particular subcutaneous tissue and musculature, and the tube has an external surface covered with a coating of titanium of sufficient thinness for the tube to retain its soft characteristics.

2. Arrangement in accordance with claim 1, wherein the tip is detachable from the tube.

* * * * *

UNITED STATES PATENT AND TRADEMARK OFFICE
CERTIFICATE OF CORRECTION

PATENT NO. : 5,613,955

DATED : March 25, 1997

INVENTOR(S) : Wadstein

It is certified that error appears in the above-identified patent and that said Letters Patent is hereby corrected as shown below:

Title Page, Col. 1, [56] References Cited: insert --4,559,039  12/85  Ash et al.  604/175-- on the line after after "European Pat. Off."

Col. 2, line 20: insert --.-- immediately after "form"

Col. 2, line 27: "la" should read --l*a*--

Col. 2, line 56, claim 1: insert --having-- after "fluid"

Signed and Sealed this

Tenth Day of March, 1998

*Attest:*

BRUCE LEHMAN

*Attesting Officer*  *Commissioner of Patents and Trademarks*